United States Patent [19]

Schammel et al.

[11] Patent Number: 5,095,141

[45] Date of Patent: Mar. 10, 1992

[54] PROCESS FOR PSEUDOCUMENE OXIDATION TO TRIMELLITIC ACID WITH MOTHER LIQUOR RECYCLE

[75] Inventors: Wayne P. Schammel; Chang-Man Park, both of Naperville; Donald E. Ruedin, Joliet; John N. Wood, Joliet; Leo C. Fende, Joliet, all of Ill.

[73] Assignee: Amoco Corporation, Chicago, Ill.

[21] Appl. No.: 629,825

[22] Filed: Dec. 19, 1990

[51] Int. Cl.$^5$ .......................................... C07C 51/265
[52] U.S. Cl. .................................. 562/414; 549/245; 562/416; 562/480
[58] Field of Search .............................. 562/414, 416

[56] References Cited

U.S. PATENT DOCUMENTS 3,161,658 12/1964 Meyer .............................. 562/414 X
4,948,921 8/1990 Green et al. ......................... 562/413

Primary Examiner—Jose G. Dees
Assistant Examiner—Vera C. Clarke
Attorney, Agent, or Firm—Gunar J. Blumberg; William H. Magidson; Ralph C. Medhurst

[57] ABSTRACT

A process is disclosed for oxidation of pseudocumene to trimellitic acid wherein process residue and bottoms from stripping procedures to recover process solvent are recycled and incorporated in filtrate mother liquor and reinjected into the oxidation reactor at a point in time at least after the first methyl group in the pseudocumene molecule has been oxidized to a carboxy group. Recovery of trimellitic acid is increased, catalyst recovery is increased in a form suitable for immediate recycle to the oxidation reaction, and waste products from the oxidation process are substantially reduced.

7 Claims, No Drawings

PROCESS FOR PSEUDOCUMENE OXIDATION TO TRIMELLITIC ACID WITH MOTHER LIQUOR RECYCLE

FIELD OF THE INVENTION

This invention relates to trimellitic acid and trimellitic anhydride and more particularly is concerned with an improved process for oxidation of pseudocumene to trimellitic acid wherein mother liquor containing catalyst and trimellitic acid is recycled to the oxidation reactor. Yield of trimellitic acid is increased over yields obtained by previous methods, catalyst is recovered and recycled, and process waste is reduced in quantity. The process has particular applicability to preparation of trimellitic acid by oxidation of pseudocumene in the presence of a heavy metal oxidation catalyst such as cobalt or manganese. Trimellitic acid is a catalyst deactivator of such catalyst and in sufficient concentrations causes catalyst precipitation. Manganese can be precipitated preferentially to cobalt but the effect is catalyst deactivation. The precipitated trimellitic acid/metal complexes cause a loss of catalyst metals and can cause plugging problems downstream in the product recovery procedures. These difficulties have prevented the utilization of any method in the prior art to recycle mother liquor from the oxidation reactor wherein the mother liquor contains soluble catalyst and soluble trimellitic acid.

BACKGROUND OF THE INVENTION

The process of this invention provides a more economical commercial process than previously available methods for the manufacture of trimellitic anhydride (4-carboxyphthalic anhydride) through the catalytic liquid phase oxidation of pseudocumene. (1,2,4-trimethylbenzene) with air in the presence of acetic acid as reaction solvent, the separation and recovery of crystalline trimellitic acid from the oxidation reaction effluent, the thermal dehydration of trimellitic acid to its anhydride, and the separation and recovery of the anhydride from intermediate oxidation by-products and other oxidation by-product impurities by distillation and/or vaporization process steps.

Pseudocumene is oxidized with air mainly to a mixture of di- and tricarboxy acids in the presence of catalysts comprising cobalt and/or manganese oxidation catalysts under liquid phase conditions, using acetic acid as the reaction solvent.

U.S. Pat. No. 4,587,350, incorporated by reference herein, discloses a process for the oxidation of pseudocumene to trimellitic acid by a catalytic oxidation of pseudocumene with air in the presence of acetic acid in an oxidation zone in the liquid phase with catalysts comprising zirconium, cobalt, and manganese and a source of bromine.

By the use of oxygen as oxidant and a combination of cobalt as metal oxidation catalyst and alpha-methylenic ketones as side chain oxidation initiator or promoter, pseudocumene is oxidized mainly to a mixture of 2-methyl terephthalic acid and 4-methyl isophthalic acid in the presence of acetic acid solvent under liquid phase conditions at atmospheric pressure. Catalytic liquid phase oxidation of pseudocumene with air can be accomplished in the presence of acetic acid solvent and catalysis provided by the combination of heavy metal oxidation catalyst and a source of bromine as disclosed and claimed in U.S. Pat. No. 2,833,816. This oxidation method using a combination of heavy metal oxidation catalyst and a source of bromine to provide catalysis describes the production of 92 weight percent trimellitic acid filter cake product in a two hour reaction at 198° C. (about 390° F.). The theoretical yield of trimellitic acid from pseudocumene is 175 weight percent. However, the oxidation method of U.S. Pat. No. 2,833,816 has been developed to produce total trimellitic acid yields in the range of 135 to 161 weight percent or about 77% to about 92% of theory based on the pseudocumene hydrocarbon feed. By total yield of trimellitic acid is meant all of the trimellitic acid in the oxidation reaction effluent.

The highly developed catalytic liquid phase air oxidation of pseudocumene by the method of U.S. Pat. No. 2,833,816 using catalysis provided by the combination of heavy metal oxidation catalysts therein defined with bromine or a source of bromine under liquid phase oxidation conditions produces total trimellitic acid yields of 135 to 161 weight percent based on commercially available pseudocumene. But, there are also co-produced trimesic acid, iso- and terephthalic acids, 4-methylorthophthalic acid, 2-methylterephthalic acid, 4-methylisophthalic acid and formyl phthalic acids in amounts as to present substantial problems in the recovery of high quality trimellitic acid, dehydration of trimellitic acid to its intramolecular anhydride and recovery of that anhydride.

Another problem in the manufacture of trimellitic acid through the oxidation of pseudocumene to trimellitic acid in the presence of acetic acid comes from the relatively high solubility of trimellitic acid in acetic acid. This solubility goes from about 1.0 pound per 100 pounds glacial acetic acid at 80° F. to 6.5 pounds per 100 pounds glacial acetic acid at 220° F. The presence of water in the acetic acid increases the solubility of trimellitic acid so that in aqueous acetic acid solvent having 82 to 85% acetic acid and 18 to 15% water by weight there are dissolved at 80° and 220° F. about 3.2 pounds and 16.5 pounds trimellitic acid per 100 pounds solvent. Ordinarily aqueous acetic acid of 90 to 98% (10 to 2% water) by weight is used in the oxidation as solvent not only because acetic acid of higher strength is more expensive to recover but also because the presence of 2 to 10% water by weight substantially eliminates oxidation induction. During oxidation of the methyl groups to carboxylic acid groups water is produced as a by-product and is generally retained through the removal of heat of reaction by condensing the acetic acid and water boilup from the liquid phase in the oxidation zone and returning the condensate to the oxidation zone. The aqueous acetic acid solvent in the effluent removed from the oxidation zone can contain about 10 to 25% water (90 to 75% acetic acid) by weight when the 90 to 98% aqueous acetic acid solvent is used in the weight ratios of 5 to 2 parts of pseudocumene. Thus, at usual crystallization temperatures of 60° to 120° F., a substantial amount of trimellitic acid remains in solution.

For example, in Example II of U.S. Pat. No. 3,161,658 there is described the cooling to 100° F. of an oxidation reaction effluent containing for each 500 parts acetic acid solvent, 200 parts trimellitic acid and 50 parts of pseudocumene oxidation intermediates. There was recovered 135 parts crystalline trimellitic acid per 500 parts of acetic acid solvent. Thus, of the originally produced 200 parts trimellitic acid there was left in solution 65 parts or 32.5%. This appears to have been an oxidation of pseudocumene conducted in the presence of acetic acid solvent in the ratio of about 3.5 parts solvent per part of pseudocumene. Higher ratios of solvent to pseudocumene would have caused a greater proportion of the total trimellitic acid to remain in solution at 100° F. For example, at a 5 to 1 solvent ratio 45% of the trimellitic acid produced would have remained in solution at crystallization and filtration temperatures of 100° F.

In manufacture of trimellitic acid, after maximizing recovery of the trimellitic acid from the acetic acid reaction solvent by crystallization and filtration, the mother liquor is stripped to recover the aqueous acetic acid solvent. The residue obtained is a mixture of trimellitic acid, oxygen-containing derivatives of benzene and toluene which are mono-, di- and tricarboxylic acids, aldehydocarboxylic acids, and methylol-substituted benzene, toluene or their carboxylic (benzoic or toluic) acids. The residue also contains components of catalysis. These components of catalysis are Co-Mn-Br or Co-Mn-Br-Zr from the liquid phase oxidation of pseudocumene. While such residue amounts to from 2 to 25 weight percent of the trimellitic acid produced, such residue production annually is substantial in view of the millions of pounds of trimellitic acid produced annually.

Since this residue contains water soluble benzene carboxylic acids and water-soluble forms of the catalyst, landfill disposal of such residue is undersirable because rain and groundwater break out these carboxylic acids and water-soluble forms of the catalyst which are typically cobalt and manganese acetates. Disposal of the organic portion of the residue can be made by processes as disclosed in U.S. Pat. Nos. 4,258,227, 4,266,084 and 4,393,264. The catalyst components in the residue are converted by the processes of these patents to forms in the resultant ash which are difficult and/or expensive to convert to reusable forms for the oxidation of the pseudocumene.

The recovery of the cobalt and manganese and zirconium, if such be present in the catalyst system, would not only reduce catalyst costs but reduce or eliminate any costs associated with disposal of the ash.

It is therefore an object of this invention to recover trimellitic acid from the stripper residue or bottoms and reduce the amount of waste products obtained in the oxidation of pseudocumene to trimellitic acid.

It is an object of the instant invention to increase the yield of trimellitic acid from oxidation of pseudocumene to trimellitic acid by increasing recovery of trimellitic acid.

It is an object of the instant invention to improve the process for preparation of trimellitic acid by oxidation of pseudocumene in presence of a cobalt-manganese or cobalt-manganese-zirconium catalyst with bromine and a solvent comprising acetic acid wherein recovery of trimellitic acid obtained thereby is increased over previously available processes and the catalyst metals are recovered in a form suitable for immediate re-use and therefore, immediate recycle to the oxidation reaction.

It is an object of the instant invention to reduce the amount of waste produced by an oxidation process to prepare trimellitic acid from pseudocumene.

Other objects of the instant invention will be apparent from the discussion which follows.

SUMMARY OF THE INVENTION

A process is disclosed for the oxidation of pseudocumene to trimellitic acid wherein recovery of trimellitic acid produced thereby is increased, catalyst is recovered in a form suitable for immediate recycle to the oxidation reaction, and waste products from the oxidation process are substantially reduced in quantity as compared with previously available processes in the prior art.

Process residue and bottoms from stripping procedures to recover process solvent are recycled to and incorporated in filtrate mother liquor and re-injected into the oxidation reactor at a point in time after initiation of an oxidation reaction and after a period of time sufficient to allow the first methyl group on the pseudocumene molecule to be oxidized to a carboxy group. Recovery of trimellitic acid is increased 8 to 10 wt%, catalyst metals recovery is improved to at least 10 wt%, and waste produced is reduced by at least 10 wt%.

BRIEF DESCRIPTION OF THE INVENTION

We have discovered an improved process for the manufacture of trimellitic acid from pseudocumene wherein mother liquor containing catalyst from the oxidation reaction and trimellitic acid solubilized in the mother liquor is recycled to the oxidation reaction. Mother liquor from the oxidation reaction has not been completely successfully recycled back to the oxidation reaction in previous attempts due to the deactivating effects of trimellitic acid upon the cobalt-manganese or cobalt-manganese-zirconium catalyst and the resulting increase in production of impurities, particularly high boiling compounds such as tetracarboxy benzenes. The improvement arises from conducting the oxidation reaction in such a procedure that the mother liquor recycle is injected into the oxidation reaction only after the oxidation reaction preferably has oxidized only the first methyl group in the pseudocumene molecule to a carboxy group. The injection of the mother liquor recycle into the oxidation reaction is at a point in time at least 5 minutes after initiation of the oxidation reaction. The mother liquor recycle can be as much as 25 to 40 wt % of the contents of the oxidation reaction mixture containing partially oxidized pseudocumene, other oxidation products and catalyst.

Because of the complexing action of trimellitic acid with a catalyst of cobalt-manganese or cobalt-manganese-zirconium to form metal complexes which precipitate, thus depriving the oxidation reaction of catalyst, the oxidation of pseudocumene to trimellitic acid with a catalyst of the above composition is preferably either in batch mode or semi/continuous mode. A semi-continuous mode is defined as a batch mode which is modified by the continuous addition of amounts of pseudocumene to preclude the continued formation of catalyst metal complexes in the presence of predominant amounts of trimellitic acid. A semi-continuous mode, as defined herein, is particularly suited for the preparation of trimellitic acid from pseudocumene in the presence of the above-described catalyst because the third methyl group tends to be oxidized sequentially to a carboxy group and thus form trimellitic acid.

Commercially available pseudocumene is not pure and contains 1 to 5 weight percent of alkyl substituted benzenes having boiling points close to that of pseudocumene such as ethyl toluenes and mesitylene $C_9$ aromatics and even some $C_8$ aromatics such as the xylenes. The ethyl toluenes and xylenes impurities are oxidized to phthalic acids and mesitylene is oxidized to trimesic acid (1,3,5-benzene tricarboxylic acid) at the same time pseudocumene is oxidized to trimellitic acid. As noted above, it is difficult to convert all of the three methyl groups of pseudocumene to carboxylic acid groups. This difficulty arises from the effect that conversion of one of the two ortho-oriented methyl groups to carboxylic acid group has on the remaining methyl group. This oxidation difficulty results in the co-production of small amounts of 4-methylorthophthalic acid, 2-methylterephthalic acid and 4-methylisophthalic acid. This oxidation difficulty is in addition to the coproduction of such next to last step oxidation by-products as the formylphthalic acids. The last oxidation step product of pseudocumene is, of course, trimellitic acid.

We have discovered an improved process for the manufacture of trimellitic acid anhydride starting with pseudocumene. The improvement arises from the discovery of a process for recovering trimellitic acid in yields in the range 80 to 90% and higher based on the total trimellitic acid produced by catalytic liquid phase air oxidation of pseudocumene in the presence of a catalysis provided by the combination of heavy metal oxidation catalyst and bromine or a source of bromine and in the presence of acetic acid solvent having 93 to 98% acetic acid and 7 to 2% water by weight. The recovery portion of the process of this invention starts with the effluent from the oxidation process which produces 135 to 162 weight percent or more trimellitic acid, based on pseudocumene oxidized with air in the presence of 2 to 5 parts of said 93 to 98% aqueous acetic acid solvent as oxidation reaction effluent. Such oxidation reaction effluents contain 182 to 338 parts aqueous acetic acid of about 10 to about 25% water (90 to 75% acetic acid) per 100 parts trimellitic acid, all by weight. Since the recovery technique of this invention is equally applicable, as will be later apparent, to oxidation reaction effluents having aqueous acetic acid solvent of such wide water variations as 10 to 25 weight percent, there is eliminated the need for having precise control over the water content of the solvent initially charged to the oxidation reaction as before thought or appeared to be needed to aid in the separation and recovery of trimellitic acid.

The suspensions of crystals formed in the crystallization zone are transferred out as feed for a means for separating solids and liquids. Such solid-liquid separation means as continuous centrifuging, filtering, settling, and the like can be used.

The mother liquor from the separation and recovery of crystalline trimellitic acid and vapor from the first acid product dehydration zone are combined as feed for a stripping zone operated at 0 to 10 psig and a feed temperature of 220° F. to 250° F. An external reboiler heats the liquid in the column to 260° F. In this manner water and acetic acid are substantially completely removed as the main feed to the acetic acid concentrator and the trimellitic acid in the stripping zone feed contained in the bottoms is transferred to the stripper stillpot. A convenient way to strip out the acetic acid and water is to use the combined acetic acid mother liquor and condensed dehydration vent vapors as feed to a distillation column whose bottoms liquid is transferred to a stillpot whose temperature is above the melting point of trimellitic anhydride, about 450° F. The bottoms from such a stripping operation are liquid.

The bottoms liquid from the stripping step contains about 5.7% of the total trimellitic acid produced by the oxidation. In the present novel process this trimellitic acid is recovered by recycling up to about 50 to about 60 weight percent, preferably about 25 weight percent of the liquid from the stripper stillpot to the oxidation reaction.

The previously mentioned starting oxidation reaction effluent is obtained by the air oxidation of pseudocumene in the presence of aqueous acetic acid solvent of less than 10 weight percent, preferably 2 to 7 weight percent, water content and in the presence of catalysis provided by the combined use of heavy metal oxidation catalyst and bromine at an oxidation temperature within the range of 320° and 410° F. and a pressure to maintain at least a liquid phase of acetic acid solvent and pseudocumene in the oxidation zone at the operating temperature. A portion of the required level of catalyst is added during the oxidation reaction as tailout catalyst to maintain the rate of oxidation. Pressures in the range of 100 to 370 psig (pounds per square inch gauge) are satisfactory for maintaining necessary liquid phase conditions in the oxidation zone at said operating temperature. The oxidation can be conducted in a batch or semi-continuous manner. As noted above, by "semicontinuous" is meant charging solvent and catalyst to an oxidation reactor and heating them to reaction temperature and pressure and then simultaneously introducing pseudocumene and air into the oxidation zone until all the hydrocarbon has been added (i.e. the continuous portion) and then continue introducing air into the oxidation zone (batchwise portion) until the oxidation of pseudocumene is substantially complete, i.e. oxygen is no longer being consumed. Semi-continuous then in part combines some features of both continuous and batchwise oxidation.

The precise conditions of operation developed for the oxidation of pseudocumene to go from 92 weight percent to 135 to 161 weight percent and higher total trimellitic acid are not material to the understanding and practice of the present invention. Also those precise operating conditions are not a part of this invention. This invention however does depend on and uses to advantage the factual existence of the ability to obtain such high conversions of pseudocumene with air as the oxidant, the use of the system of catalyst provided by the combination of heavy metal oxidation catalyst and bromine as taught in U.S. Pat. No. 2,833,816, the use of acetic acid solvent having 95 to 98% acetic acid and 5 to 2% water by weight and the conditions of temperature and pressure before mentioned for liquid phase operation. This high conversion oxidation, then, is the starting process step in the combination of process steps that make the total process for obtaining high purity trimellitic acid in high yields based on the total trimellitic acid produced.

For the understanding and practice of the present invention it is necessary to know the amounts of aromatic co-products and by-products also present in the oxidation reaction effluent. These aromatic co-products and by-products can be specifically identified by types. Most useful for the understanding and practice of this invention is not the precise amount of each specific aromatic co-product and by-product, but rather, the weight ratio of the total of said aromatic by-products and co-products related to the trimellitic acid present in the oxidation reaction effluent. The total weight of said aromatic co-products and by-products can be in the ratio range of from 5 to 25 parts per 100 parts of trimellitic acid by weight.

DESIRABLE OPERATING CONDITIONS

Desirable operating conditions for the process steps of this invention are given in the following description. Oxidation reaction effluent is obtained by the oxidation of pseudocumene(PSC) with air in an oxidation zone at 320° to 410° F. and 100 to 370 psig in the presence of 0.5 to 5.0 parts inclusive of 94 to 98% aqueous acetic acid (6 to 2% water) per part of pseudocumene of 97 to 99% by weight purity in the presence of heavy metals (e.g. supplied as zirconium acetate, and cobalt and manganese acetate tetrahydrates) in a total concentration of 0.06 to 0.3 weight percent as metals and bromide as provided by hydrogen bromide, sodium bromide, and/or tetrabromoethane in a bromine concentration of 0.1 to 0.7 weight percent. The weight percent of catalyst components are based on the acetic acid solvent. The resulting oxidation effluent withdrawn from the oxidation zone is at 400° to 410° F. and contains trimellitic acid(TMLA) in an amount equivalent to 1.35 to 1.61 pounds per pound of pseudocumene and aromatic impurities in the range of 30 to 5 pounds per 100 pounds of trimellitic acid.

A slurry of trimellitic acid crystals of from 40 to 60% crystal solids by weight is obtained depending upon the portion of water and acetic acid vaporized and removed from a crystallization zone.

The slurry from the crystallization zone is continuously transferred to a rotary vacuum filter, centrifugal filter, or filter press and trimellitic acid crystal cake is separated at 100° F. to 130° F. The mother liquor is collected in a surge drum. The filter cake contains 15 to 35% acetic acid.

The acetic acid wet filter cake is continuously charged by screw conveyor to a boiler at about 450° F. and pressures at a range of about 10 to 25 psig. The hold time in the boiler is about 1 to 2 hours which is sufficient time to assure removal of acetic acid as vapors. These vapors are transferred to the stripper feed vessel and combined with the mother liquor. The mother liquor from the stripper stillpot containing trimellitic acid and catalyst as well as acetic acid from the filter cake is transferred to a mother liquor charge drum to be mixed with mother liquor from the filter press, centrifugal filter or rotary vacuum filter. The mother liquor containing the trimellitic acid, catalyst, acetic acid and soluble oxidation reaction by-products are re-injected into the oxidation reaction in a ratio of from about 10 wt % to about 60 wt % of the pseudocumene and partially oxidized pseudocumene present in the oxidation reaction. The re-injection of the mother liquor into the oxidation reaction can reduce the need for addition of tailout catalyst during the oxidation reaction.

In the process of the instant invention, the combined acetic acid mother liquor and vent vapor from the first acid product dehydrator and other aqueous acetic acid liquors collected in the surge drum following filtration to recover trimellitic acid crystals is continuously charged to a stripping zone of about 220° F. to about 270° F. where substantially all of the water and acetic acid are vaporized and sent as vapor or condensate feed to a fractionation zone to concentrate to acetic acid of 94 to 98% by weight. The residue in the stripper bottoms is liquid. This liquid is heated to a temperature in a range of about 430° F. to 470° F. in the stripper stillpot operated at about 10-25 psia. The stripper stillpot bottoms contains 30 to 60% trimellitic acid. In a process of this invention up to about 50% or 60% of this residue is charged to the mother liquor charge drum.

This type of oxidation reaction effluent, the dehydration-drying of acetic acid wet trimellitic acid, stripping of combined acetic acid mother liquor to obtain stripper residue, the recycle of residue from the stripper stillpot to the mother liquor charge drum and recycle of bottoms from the stripper stillpot, all cooperate with the preceding and following steps to provide ultimately the recovery of about 90% of the total trimellitic acid first produced. The combination of these steps is essential for this result. The following illustrative examples will demonstrate operation of the total process of this invention under preferred conditions.

EXAMPLE I

Pseudocumene (PSC) was oxidized in a 2-liter titanium steel reactor equipped with internal stirring mechanism and external heating jacket. A mixture of pseudocumene (225 g) with 420 g of 95% acetic acid was heated to a temperature of 320° F. (160° C.) at which point air was injected into the reaction mixture at a rate of 0.8 standard cubic feet per minute, in the presence of cobalt and manganese acetates, hydrogen bromide and zirconium acetate. Concentration of cobalt was 0.175 wt %, manganese 0.084 wt %, zirconium 0.004 wt %, based on pseudocumene. Enough hydrogen bromide was added to equal a 0.7 to 1.0 molar bromine to metals ratio, but only 20% of the total bromine was added at the beginning of the oxidation. The remainder was added gradually over the period of the oxidation together with additional manganese (0.01 wt %) and zirconium (0.005%) as tailout catalyst.

The temperature was gradually increased from 320° F. (160° C.) to 410° F. (210° C.) over the reaction period of 60 minutes. Pressure was also increased from about 150 psig to about 400 psig over the same period. After the completion of the oxidation, as measured by percent oxygen in the vent gas from the reaction, injection of the air was discontinued, the contents of the reactor were collected and analyzed by gas chromatography and liquid chromatography analysis. Details are in Table I.

EXAMPLE II

The procedure of Example I was repeated except that 200 ml of mother liquor from the stripper stillpot of a commercial trimellitic acid product unit of Amoco Chemical Company, Chicago, Ill., was added to the oxidation reaction at a rate of 5 ml per minute from 20 to 60 minutes into the oxidation reaction. After the completion of the oxidation, the contents of the reactor were collected and analyzed by gas chromatography and liquid chromatography analysis. Details are in Table I.

EXAMPLE III

The procedure of Example I was repeated except that catalyst metals loadings were adjusted to compensate for the additional metals added in the mother liquor. The initial charge was 1.47 g cobalt acetate (0.35 g Co), 0.78 g manganese acetate (0.18 g Mn) and no zirconium. The solvent was reduced to 300 g of 95% acetic acid. Mother liquor of 200 ml, was added to the initial reactor charge before the oxidation reaction initiated. After the oxidation, the contents of the reactor were analyzed by gas chromatography and liquid chromatography analysis. Details are in Table I.

EXAMPLE IV

In the procedure of Example I, the same solvent and catalyst levels as in Example III were added to the reactor. Mother liquor 237 g, but containing the same catalyst metals content as Example III, was added to the reaction at a rate of 5.25 ml/min from 5 to 50 minutes into the reactor oxidation. No other catalyst was added. Results of the procedure are in Table I.

EXAMPLE V

In the procedure of Example I, Example I was repeated except that 5 g of trimellitic acid (TMLA) were added to the initial reaction charge. The analysis indicated that the burning of the charge stock was increased. Details are in Table I.

EXAMPLE VI

The procedure of Example I was repeated except that 20 g of trimellitic acid (TMLA) were added to the charge stock. In this procedure, the burning of the charge stock was increased over that of Example V. The yield is also very low which indicates the trimellitic acid was being destroyed and that additional burning of the oxidation intermediates was occurring.

TABLE I

PSEUDOCUMENE OXIDATION WITH RECYCLE OF MOTHER LIQUOR CONTAINING RESIDUE FROM SOLVENT STRIPPER

| | Examples | | | | | |
|---|---|---|---|---|---|---|
| | I | II | III | IV | V | VI |
| Oxidation Reactor Charge | | | | | | |
| PSC, g | 225 | 225 | 225 | 225 | 225 | 225 |
| TMLA, g | — | — | — | — | 5 | 20 |
| Co, wt % | 0.175 | 0.175 | 0.155 | 0.155 | 0.175 | 0.175 |
| Mn, wt % | 0.084 | 0.084 | 0.078 | 0.078 | 0.084 | 0.084 |
| Zr, wt % | 0.004 | 0.004 | — | — | 0.004 | 0.004 |
| HBr/PSC mole ratio | 0.7/1.0 | 0.7/1.0 | 0.7/1.0 | 0.7/1.0 | 0.7/1.0 | 0.7/1.0 |
| Acetic Acid, g | 420 | 420 | 300 | 300 | 420 | 420 |
| Tailout Catalyst Added | | | | | | |
| Mn, wt % | 0.01 | 0.01 | 0.01 | 0.01 | 0.01 | 0.01 |
| Zr, wt % | 0.005 | 0.005 | 0.005 | 0.005 | 0.005 | 0.005 |
| Mother Liquor Added, ml | — | 200 | 200 | 237* | — | — |
| Co, wt % | — | 0.020 | 0.020 | 0.020 | — | — |
| Mn, wt % | — | 0.006 | 0.006 | 0.006 | — | — |
| Zr, wt % | — | 0.004 | 0.004 | 0.004 | — | — |
| Oxidation Reactor Products | | | | | | |
| CO + $CO_2$, mole % | 4.3 | 4.7 | 6.4 | 5.8 | 5.7 | 10.0 |
| TMLA, wt % | 90.9 | 89.4 | 87.9 | 87.3 | 90.5 | 89.5 |
| High Boilers, wt % | 2.02 | 3.25 | 3.71 | 3.11 | 2.71 | 2.88 |
| Low Boilers, Dibasic Acids, wt % | 1.71 | 3.52 | 3.37 | 4.98 | 2.89 | 3.28 |
| Methyl Dibasics, wt % | 0.33 | 0.33 | 0.42 | 0.29 | 0.27 | 0.12 |
| Run Time, min. | 64 | 62 | 74 | 68 | 60 | 67 |
| Yield, g TMLA/g PSC | 1.42 | 1.52 | 1.40 | 1.43 | 1.43 | 1.31 |

TABLE I-continued

PSEUDOCUMENE OXIDATION WITH RECYCLE OF MOTHER LIQUOR CONTAINING RESIDUE FROM SOLVENT STRIPPER

| | Examples | | | | | |
|---|---|---|---|---|---|---|
| | I | II | III | IV | V | VI |
| Yield, TMLA, mole % | 81.1 | 86.8 | 80.0 | 81.7 | 81.7 | 74.8 |
| Solids Recovered, g | 352.7 | 383.8 | 358.2 | 369.7 | 356.0 | 330.5 |
| TMLA Recovered, g | 320.6 | 343.1 | 314.9 | 322.8 | 322.2 | 295.8 |

*Volume increased by addition of water

The data in Table I indicate the improved yields, in mole %, obtained by the process of the instant invention. Example I illustrates results of a conventional oxidation wherein mother liquor recycle material is not injected into the oxidation reaction. Example II illustrates the improved recovery of trimellitic acid (TMLA) over the recovery illustrated by Example I, wherein the mother liquor is added to the reaction 20 minutes after the start of the reaction. Example III illustrates the loss in recovery of trimellitic acid occasioned by a longer run time which indicates a poisoning of the catalyst caused by formation of a trimellitic acid/catalyst complex because the mother liquor was added to the reaction mixture with the initial charge of the reactants to the reactor. In Example IV, the run time was greater than in Example II because the initial catalyst loading was reduced to allow for the addition of the mother liquor catalyst metals. In Example V, excess trimellitic acid was added to the reaction of Example I. The result was increased burning of the trimellitic acid present in the oxidation reaction, as evidenced by the increase in the amount of $CO + CO_2$ in Example V versus that of Example I. An additional amount of trimellitic acid, 20 g, was added to the reaction of Example VI. In this example, the production of $CO + CO_2$ is very high and the yield of trimellitic acid is very low, which indicates the trimellitic acid is being destroyed and the reaction is causing additional burning of oxidation intermediates.

In all examples, the levels produced of methyl dibasics were low and statistically undistinguishable from each other. The low levels indicate the degree to which each reaction went to completion.

The above data indicate that the addition of trimellitic acid or mother containing trimellitic acid early in the oxidation cycle causes additional burning which lowers yield of trimellitic acid and increased by-product formation. The data also indicate that adding the mother liquor later in the oxidation cycle circumvents these reaction results and permits effective mother liquor recycle with attendant increased recovery of product.

EXAMPLE VII

In the procedure of Example I, pseudocumene was oxidized. Samples were taken at 10 minute intervals and analyzed by gas chromatography and liquid chromatography. Details are in Table II as to the primary components of the oxidation mixture present after each 10 minute interval. The presence of the dimethylbenzoic acid compounds and its precursors are present in a significant amount after 10 minutes of oxidation time. After 20 minutes oxidation time, the dimethylbenzoic acid and its precursors decrease in amount and the amounts of di- and tribasic acids begin to increase in amount. After 50 minutes of oxidation time, trimellitic acid was present in substantial amount and the amounts of mono- an dibasic acids were significantly decreased.

TABLE II

Pseudocumene, Oxidation Intermediates and By-Products Present In Interrupted Oxidations

| Components, wt. % | 10 Minute Intervals | | | | | |
|---|---|---|---|---|---|---|
| | 10 | 20 | 30 | 40 | 50 | 60 |
| Pseudocumene | 12.7 | 1.67 | 0.06 | nd | nd | nd |
| Dimethylbenzoic Acid and Precursors | 18.39 | 21.10 | 9.37 | 0.77 | 0.07 | 0.05 |
| 4-Methyl Phthalic Acid | 0.28 | 1.49 | 4.24 | 6.81 | 1.59 | 0.06 |
| 4-Methyl Isophthalic Acid | 0.12 | 0.91 | 3.55 | 4.15 | 0.45 | 0.05 |
| 2-Methyl Terephthalic Acid | 0.17 | 1.08 | 4.31 | 5.88 | 0.66 | 0.07 |
| Phthalic Acid | 0.09 | 0.07 | 1.44 | 0.24 | 0.40 | 0.36 |
| Isophthalic Acid | 0.02 | 0.03 | 0.07 | 0.11 | 0.20 | 0.21 |
| Terephthalic Acid | 0.02 | 0.03 | 0.06 | 0.08 | 0.15 | 0.16 |
| Tetracarboxybenzenes | 0.06 | 0.22 | 0.02 | 0.03 | 0.17 | 0.39 |
| Other High Boilers | 0.12 | 0.82 | 0.73 | 2.08 | 0.81 | 0.53 |
| TMLA | 0.02 | 0.04 | 0.78 | 8.05 | 28.8 | 35.3 |
| Acetic Acid | 56.8 | 54.7 | 56.3 | 49.8 | 46.9 | 47.4 |
| Water | 7.7 | 10.2 | 12.7 | 14.3 | 15.4 | 15.6 |

Note:
nd — Not Detected
TMLA — Trimellitic Acid

The above data indicate that the oxidation of pseudocumene takes place in steps and that the production of trimellitic anhydride is a function of reaction time.

EXAMPLE VIII

The procedure of Example I was repeated except that 15 g of effluent solids from a commerical trimellitic acid product unit of Amoco Chemical Company, Chicago, Ill. was added to the initial reactor charge. Although no analysis was made of the effluent, a typical analysis of a mother liquor and stripper stillpot bottoms available from the same commercial unit indicates compounds present in such an effluent. Details of typical analyses of mother liquor and stripper stillpot bottoms as to primary components are in Table III. Details of the results of adding an effluent from a commercial trimellitic acid product unit are in Table IV.

TABLE III

Composition of Mother Liquor and Stripper Stillpot Bottoms

| Wt % | Mother Liquor | Stripper Stillpot Btms |
|---|---|---|
| Dimethylbenzoic acids | 0.013 | 0.13 |
| Phthalic Acid | 0.114 | 3.89 |
| Terephthalic Acid | 0.019 | 0.49 |
| Isophthalic Acid | 0.060 | 1.62 |
| Methyl dibasic acids | 0.038 | 0.69 |
| Other Mono- and DiBasic Acids | 0.031 | 3.52 |
| Trimellitic Acid | 3.90 | 6.12 |
| Tetracarboxybenzenes | 0.115 | 2.99 |
| Other High Boilers | 0.241 | 10.2 |
| Cobalt | 0.018 | 0.80 |
| Manganese | 0.010 | 0.45 |
| Zirconium | 0.001 | 0.07 |
| Bromine | 0.034 | 1.14 |
| Acetic Acid | 71.1 | — |
| Water | 23.7 | — |

TABLE IV

Results of Adding Reactor Effluent to Pseudocumene Oxidation

| Solids Recovered Wt % | Example I | Example VIII |
|---|---|---|
| TMLA | 90.9 | 89.2 |
| Phthalic Acid | 0.62 | 1.13 |
| Terephthalic Acid | 0.46 | 1.04 |
| Isophthalic Acid | 0.38 | 1.02 |
| Methyl Dibasics | 0.33 | 0.24 |
| Other Low Boilers | 0.65 | 0.73 |
| High Boilers | 2.02 | 3.60 |
| CO + CO2, mole % | 4.3 | 11.7 |
| Run Time, min | 64 | 73 |
| Solids Recovered, g | 352.7 | 299.0 |
| TMLA Recovered, g | 320.6 | 266.7 |
| Yield g TMLA/g PSC | 1.42 | 1.19 |
| Yield, TMLA mole % | 81.1 | 68.0 |

The above data indicate that addition of reactor effluent to the oxidation reactor has an extremely adverse effect upon the oxidation of pseudocumene when added to the reactor charge before the initiation of the reaction. The typical analyses, as presented in Table III, indicate the components present in the effluent added to the reactor.

That which is claimed is:

1. An improved process for the preparation of trimellitic acid from pseudocumene by catalytic air oxidation of said pseudocumene in the presence of a heavy metal catalyst and acetic acid in an oxidation zone wherein liquid-phase conditions are maintained, wherein the weight ratio of acetic acid to pseudocumene is in the range of from about 0.5–5.0:1.0, the catalyst comprises one or more heavy metal oxidation catalysts comprising zirconium, cobalt and manganese and provides from about 0.1 to about 0.4 weight percent total metals based on pseudocumene, including the amount of catalyst added during the reaction as tailout catalyst to maintain the rate of reaction, and a source of bromine to provide a total of about 0.1 to about 0.3 weight percent total bromine based on pseudocumene, wherein the total weight ratio of bromine ions to total metal ions is about 0.5 to about 2.0, the zirconium content is about 1 to about 5 wt %, the manganese content is about 14 to about 60 wt %, the cobalt content is about 35 to about 80 weight percent, each metal by weight of the total metals, temperatures in the oxidation are in the range of from about 220° F. to about 480° F., reaction pressure is in the range from 100 psig to about 370 psig, wherein process residue and bottoms from stripping procedures are injected into the oxidation reaction after the initiation of the oxidation reaction and essentially after a period of time sufficient to allow the first methyl group on the pseudocumene molecule to be oxidized to a carboxy group, cooling the oxidation reaction effluent to crystallize trimellitic acid, separating and recovering crystallized trimellitic acid from the acetic acid solvent mother liquor distilling from the acetic acid mother liquor to obtain a mixture of acetic acid and water for concentration of the acetic acid content to provide acetic acid solvent concentrate for recycle to the oxidation and to obtain a stripper bottoms product in a mother liquor from which water and acetic acid have been removed, and recycling the said stripper bottoms product and said mother liquor to said oxidation reaction to inject said mother liquor and said stripper bottoms product as said process residue and bottoms from said stripping procedures into said oxidation reaction after said initiation of said oxidation reaction.

2. The process of claim 1 wherein said process residue and said stripper bottoms are injected into said oxidation reaction at a time at least five minutes after initiation of said oxidation reaction.

3. The process of claim 1 wherein said process is a batch reaction.

4. The process of claim 1 wherein said process is a semicontinuous reaction.

5. An improved process for the preparation of trimellitic acid from pseudocumene by catalytic air oxidation of said pseudocumene in the presence of a heavy metal catalyst and acetic acid in an oxidation zone wherein liquid-phase conditions are maintained, wherein the weight ratio of acetic acid to pseudocumene is in the range of from about 0.5–5.0:1.0, the catalyst comprises one or more heavy metal oxidation catalysts comprising zirconium, cobalt and manganese and provides from about 0.1 to about 0.4 weight percent total metals based on pseudocumene, including the amount of catalyst added during the reaction as tailout catalyst to maintain the rate of reaction, and a source of bromine to provide a total of about 0.1 to about 0.3 weight percent total bromine based on pseudocumene, wherein the total weight ratio of bromine ions to total metal ions is about 0.5 to about 2.0, the zirconium content is about 1 to about 5 wt %, the manganese content is about 14 to about 60 wt %, the cobalt content is about 35 to about 80 weight percent, each metal by weight of the total metals, temperatures in the oxidation are in the range of from about 220° F. to about 480° F., reaction pressure is in the range from 100 psig to about 370 psig, wherein process residue and bottoms from stripping procedures are injected into the oxidation reaction after the initiation of the oxidation reaction and essentially after a period of time sufficient to allow the first methyl group on the pseudocumene molecule to be oxidized to a carboxy group, cooling the oxidation reaction effluent to crystallize trimellitic acid, separating and recovering crystallized trimellitic acid from the acetic acid solvent mother liquor distilling from the acetic acid mother liquor to obtain a mixture of acetic acid and water for concentration of the acetic acid content to provide acetic acid solvent concentrate for recycle to the oxidation and to obtain a stripper bottoms product in a mother liquor from which water and acetic acid have been removed, and recycling the said stripper bottoms product and said mother liquor to said oxidation reaction to inject said mother liquor and said stripper bottoms product as said process residue and bottoms from said stripping procedures into said oxidation reaction after said initiation of said oxidation reaction wherein up to 50 to 60 weight percent of the liquid from stipper stillpot is recycled to said oxidation reaction.

6. An improved process for the preparation of trimellitic acid from pseudocumene by catalytic air oxidation of said pseudocumene in the presence of a heavy metal catalyst and acetic acid in an oxidation zone wherein liquid-phase conditions are maintained, wherein the weight ratio of acetic acid to pseudocumene is in the range of from about 0.5–5.0:1.0, the catalyst comprises one or more heavy metal oxidation catalysts comprising zirconium, cobalt and manganese and provides from about 0.1 to about 0.4 weight percent totals metals based on pseudocumene, including the amount of catalyst added during the reaction as tailout catalyst to maintain the rate of reaction, and a source of bromine to provide a total of about 0.1 to about 0.3 weight percent total bromine based on pseudocumene, wherein the total weight ratio of bromine ions to total metal ions is about 0.5 to about 2.0, the zirconium content is about 1 to about 5 wt %, the manganese content is about 14 to about 60 wt %, the cobalt content is about 35 to about 80 weight percent, each metal by weight of the total metals, temperatures in the oxidation are in the range of from about 220° F. to about 480° F., reaction pressure is in the range from 100 psig to about 370 psig, wherein process residue and bottoms from stripping procedures are injected into the oxidation reaction after the initiation of the oxidation reaction and essentially after a period of time sufficient to allow the first methyl group on the pseudocumene molecule to be oxidized to a carboxy group, cooling the oxidation reaction effluent to crystallize trimellitic acid, separating and recovering crystallized trimellitic acid from the acetic acid solvent mother liquor distilling from the acetic acid mother liquor to obtain a mixture of acetic acid and water for concentration of the acetic acid content to provide acetic acid solvent concentrate for recycle to the oxidation and to obtain a stripper bottoms product in a mother liquor from which water and acetic acid have been removed, and recycling the said stripper bottoms product and said mother liquor to said oxidation reaction to inject said mother liquor and said stripper bottoms product as said process residue and bottoms from said stripping procedures into said oxidation reaction after said initiation of said oxidation reaction wherein mother liquor containing trimellitic acid, said catalyst, acetic acid and soluble oxidation by-products is injected into said oxidation reaction in a ratio of from about 10 wt % to about 60 wt % of the pseudocumene and partially oxidized pseudocumene present in the oxidation reaction.

7. An improved process for the preparation of trimellitic acid from pseudocumene by catalytic air oxidation of said pseudocumene in the presence of a heavy metal catalyst and acetic acid in an oxidation zone wherein liquid-phase conditions are maintained, wherein the weight ratio of acetic acid to pseudocumene is in the range of from about 0.5–5.0:1.0, the catalyst comprises one or more heavy metal oxidation catalysts comprising zirconium, cobalt and manganese and provides from about 0.1 to about 0.4 weight percent total metals based on pseudocumene, including the amount of catalyst added during the reaction as tailout catalyst to maintain the rate of reaction, and a source of bromine to provide a total of about 0.1 to about 0.3 weight percent total bromine based on pseudocumene, wherein the total weight ratio of bromine ions to total metal ions is about 0.5 to about 2.0, the zirconium content is about 1 to about 5 wt %, the manganese content is about 14 to about 60 wt %, the cobalt content is about 35 to about 80 weight percent, each metal by weight of the total metals, temperatures in the oxidation are in the range of from about 220° F. to about 480° F., reaction pressure is in the range from 100 psig to about 370 psig, wherein process residue and bottoms from stripping procedures are injected into the oxidation reaction after the initiation of the oxidation reaction and essentially after a period of time sufficient to allow the first methyl group on the pseudocumene molecule to be oxidized to a carboxy group, cooling the oxidation reaction effluent to crystallize trimellitic acid, separating and recovering crystallized trimellitic acid from the acetic acid solvent mother liquor distilling from the acetic acid mother liquor to obtain a mixture of acetic acid and water for concentration of the acetic acid content to provide acetic acid solvent concentrate for recycle to the oxidation and to obtain a stripper bottoms product in a mother liquor from which water and acetic acid have been removed, and recycling the said stripper bottoms product and said mother liquor to said oxidation reaction to inject said mother liquor and said stripper bottoms product as said process residue and bottoms from said stripping procedures into said oxidation reaction after said initiation of said oxidation reaction wherein injection of said mother liquor containing trimellitic acid, said catalyst, acetic acid and soluble oxidation by-products is injected into said oxidation reaction in an amount sufficient to reduce the amount of said catalyst added as tailout catalyst during the oxidation reaction to maintain the rate of reaction.

* * * * *

UNITED STATES PATENT OFFICE
CERTIFICATE OF CORRECTION

Patent No. 5,095,141  Dated  March 10, 1992

Inventor(s) WAYNE P. SCHAMMEL, CHANG-MAN PARK, DONALD E. RUEDIN, JOHN N. WOOD and LEO C. FENDE It is certified that error appears in the above-identified patent and that said Letters Patent is hereby corrected as shown below:

| Col. | Line | |
|------|------|---|
| 2 | 57 | "5 to 2 parts of pseudocumene" should read --5 to 2 parts per part of pseudocumene-- |
| 13 | 52 | "liquid from stipper" should read --liquid from stripper-- |

Signed and Sealed this

Twenty-first Day of September, 1993

Attest:

BRUCE LEHMAN

Attesting Officer    Commissioner of Patents and Trademarks